United States Patent
Shoelson

(10) Patent No.: US 6,468,755 B1
(45) Date of Patent: Oct. 22, 2002

(54) METHOD FOR IDENTIFYING COMPOUNDS FOR TREATMENT OF INSULIN RESISTANCE

(75) Inventor: Steven Shoelson, Natick, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 14 days.

(21) Appl. No.: 09/636,150

(22) Filed: Aug. 10, 2000

Related U.S. Application Data

(60) Provisional application No. 60/148,037, filed on Aug. 10, 1999.

(51) Int. Cl.[7] ........................ G01N 33/53; C12N 11/00; A61K 38/00
(52) U.S. Cl. ........................ 435/7.1; 435/7.8; 435/174; 514/2
(58) Field of Search ................ 435/7.1, 7.8, 325, 435/174; 514/2, 12

(56) References Cited

U.S. PATENT DOCUMENTS

| | | | |
|---|---|---|---|
| 5,759,787 A | 6/1998 | Strulovici | 435/7.4 |
| 5,776,717 A | 7/1998 | Cao | 435/15 |
| 5,843,721 A | 12/1998 | Rothe et al. | 435/69.2 |
| 5,844,073 A | 12/1998 | Rothe et al. | 530/300 |
| 5,851,812 A | 12/1998 | Goeddel et al. | 435/194 |
| 5,854,003 A | 12/1998 | Rothe et al. | 435/7.8 |
| 5,916,760 A | 6/1999 | Goeddel et al. | 435/15 |
| 5,932,425 A | 8/1999 | Alkalay et al. | 435/7.1 |
| 5,939,302 A | 8/1999 | Goeddel et al. | 435/194 |
| 5,972,674 A | 10/1999 | Mercurio et al. | 435/194 |

FOREIGN PATENT DOCUMENTS

| | | |
|---|---|---|
| WO | WO 98/08955 | 3/1998 |
| WO | WO 98/37228 | 8/1998 |
| WO | WO 99/01541 | 1/1999 |

OTHER PUBLICATIONS

Yuan et al. Reversal of Obesity–and Diet–Induced Insulin Resistance with Salicylates or Targeted Disruption of IKKB. Science 293: 1673–1677 (2001).*
Kim et al. Prevention of fat–induced insulin resistance by salicylate. J. Clin. Invest. 108/3: 437–446 (2001).*
Newman et al., "Aspirin Causes Tissue Insensitivity to Insulin in Normal Man", *Journal of Clinical Endocrinology and Metabolism*, 57:1102–1106, 1983.
Rothwarf et al., "IKK–γ is an essential regulatory subunit of the IkB kinase complex", *Nature*, 395–297–300, Sep., 1998.
Steinberg, "Meeting Report of the ASPET–Ray Fuller Symposium: Insulin Resistance in Diabetes and Hypertension: Syndrome X and Beyond", *The Journal of Pharmacology and Experimental Therapeutics*, 294:402–406, Apr., 2000.
Yin et al, "The anti–inflammatory agents aspirin and salicylate inhibit the activity of I(kappa)B kinase–beta", 396(6706):77–80, 1998, Nature.

* cited by examiner

Primary Examiner—Gary L. Kunz
Assistant Examiner—Regina M. DeBerry
(74) Attorney, Agent, or Firm—Fish & Richardson PC

(57) ABSTRACT

The invention features a method of identifying, evaluating or making a compound or agent, e.g., a candidate compound or agent, for treatment of a disorder characterized by insulin resistance. The method includes evaluating the ability of a compound or agent to interact with, e.g., bind, IKK-β, to thereby identify a compound or agent for the treatment of a disorder characterized by insulin resistance. The invention also features compounds for treating insulin resistance identified by such methods, and methods of treating a subject having a disorder characterized by insulin resistance by administering such agents.

12 Claims, No Drawings

METHOD FOR IDENTIFYING COMPOUNDS FOR TREATMENT OF INSULIN RESISTANCE

CROSS REFERENCE TO RELATED APPLICATIONS

This application claims the benefit of U.S. Provisional Application Serial No. 60/148,037, filed on Aug. 10, 1999, which is incorporated herein by reference in its entirety.

The present invention is based, in part, on the discovery that aspirin reverses insulin resistance in liver and fat cells, e.g., by targeting IKK-β. Thus, IKK-β was discovered as a target for identifying compounds for the treatment of disorders associated with insulin resistance.

Accordingly, in one aspect, the invention features a method of identifying, evaluating or making a compound or agent, e.g., a candidate compound or agent, for treatment of a disorder characterized by insulin resistance. The method includes evaluating the ability of a compound or agent to interact with, e.g., bind, IKK-β, to thereby identify a compound or agent for the treatment of a disorder characterized by insulin resistance.

In a preferred embodiment, the disorder is diabetes, e.g., Type I or Type II diabetes, obesity, polycystic ovarian disease or syndrome X.

In a preferred embodiment, the compound is: a polypeptide, e.g., a randomly generated polypeptide which binds IKK-β; an antibody, e.g., an intrabody or a randomly generated antibody which binds IKK-β; a small molecule, e.g., a small molecule which binds IKK-β.

In a preferred embodiment, the method further includes contacting the identified compound with IKK-β, e.g., purified IKK-β, to thereby evaluate binding between the compound and IKK-β.

In a preferred embodiment, the method further includes contacting the identified compound with a cell, e.g., a fat cell or a liver cell, to thereby evaluate the effect of the compound on an IKK-β activity of the cell. For example, the ability of the compound to modulate, e.g., reduce or reverse, insulin resistance in a cell.

In a preferred embodiment, the method further includes administering the identified compound to a subject to, evaluate the effect of the compound on insulin resistance. In a preferred embodiment, the subject is a mouse (e.g., a NOD mouse, an ob/ob mouse, a db/db mouse) or a rat (e.g., a Zucker fatty rat, a streptozotocin rat).

In another aspect, the invention features a method of identifying a compound or agent for treatment of a disorder characterized by insulin resistance. The method includes contacting IKK-β, or a cell expressing IKK-β with a test compound; and determining whether the test compound binds to IKK-β, to thereby identify a compound.

Methods for identifying a compound or an agent can be performed, for example, using a cell free assay. For example, the IKK-β can be immobilized to a suitable substrate, e.g., glutathoine sepharose beads or glutathoine derivatized microtiter plates, using a fusion protein which allows for IKK-β to bind to the substrate, e.g., a glutathoine-S-transferase/IKK-β fusion protein.

In a preferred embodiment, the ability of a test compound to bind IKK-β can be determined by detecting the formation of a complex between IKK-β and the compound. The presence of the compound in complex indicates the ability to bind IKK-β.

In a preferred embodiment, IKK-β is further contacted with aspirin.

In another preferred embodiment, a compound is identified using a cell based assay. These methods include identifying a compound based on its ability to modulate, e.g., inhibit, an IKK-β activity of the cell. For example, the ability of a compound to modulate, e.g., reduce or reverse, insulin resistance in a cell, e.g., a fat cell or a liver cell, can be determined.

In a preferred embodiment, the method further includes contacting the identified compound with IKK-β, e.g., purified IKK-β, to thereby evaluate binding between the compound and IKK-β.

In a preferred embodiment, the method further includes contacting the identified compound with a cell, e.g., a fat cell or a liver cell, to thereby evaluate the effect of the compound on an IKK-β activity of the cell. For example, the ability of the compound to modulate, e.g., reduce or reverse, insulin resistance in a cell can be evaluated.

In a preferred embodiment, the method further includes administering the identified compound to a subject to evaluate the effect of the compound on insulin resistance. In a preferred embodiment, the subject is a mouse (e.g., a NOD mouse, an ob/ob mouse, a db/db mouse) or a rat (e.g., a Zucker fatty rat, a streptozotocin rat).

In a preferred embodiment, the compound is: a polypeptide, e.g., a randomly generated polypeptide which interacts with, e.g., binds, IKK-β; an antibody, e.g., an intrabody or a randomly generated antibody which interacts with IKK-β; a small molecule, e.g., a small molecule which interacts with IKK-β.

In a preferred embodiment, the compound is a compound other than aspirin.

In a preferred embodiment, the disorder is diabetes, e.g., Type I or Type II diabetes, obesity, polycystic ovarian disease or syndrome X.

In another aspect, the invention features a method of identifying a compound or agent for treatment of diabetes, e.g., Type I or Type II diabetes. The method includes contacting IKK-β, or a cell expressing IKK-β with a test compound; and determining whether the test compound binds to IKK-β, to thereby identify a compound for treatment of diabetes.

Methods for identifying a compound or an agent can be performed, for example, using a cell free assay. For example, the IKK-β can be immobilized to a suitable substrate, e.g., glutathoine sepharose beads or glutathoine derivatized microtiter plates, using a fusion protein which allows for IKK-β to bind to the substrate, e.g., a glutathoine-S-transferase/IKK-β fusion protein.

In a preferred embodiment, the ability of a test compound to bind IKK-β can be determined by detecting the formation of a complex between IKK-β and the compound. The presence of the compound in complex indicates the ability to bind IKK-β.

In a preferred embodiment, IKK-β is further contacted with aspirin.

In another preferred embodiment, a compound is identified using a cell based assay. These methods include identifying a compound based on its ability to modulate, e.g., inhibit, an IKK-β activity of the cell. For example, the ability of a compound to modulate, e.g., reduce or reverse, insulin resistance in a cell, e.g., a fat cell or a liver cell, can be determined.

In a preferred embodiment, the method further includes contacting the identified compound with IKK-β, e.g., purified IKK-β, to thereby evaluate binding between the compound and IKK-β.

In a preferred embodiment, the method further includes contacting the identified compound with a cell, e.g., a fat cell or a liver cell, to thereby evaluate the effect of the compound on an IKK-β activity of the cell. For example, the ability of the compound to modulate, e.g., reduce or reverse, insulin resistance in a cell.

In a preferred embodiment, the method further includes administering the identified compound to a subject to evaluate the effect of the compound on insulin resistance. In a preferred embodiment, the subject is a mouse (e.g., a NOD mouse, an ob/ob mouse, a db/db mouse) or a rat (e.g., a Zucker fatty rat, a streptozotocin rat).

In a preferred embodiment, the compound is: a polypeptide, e.g., a randomly generated polypeptide which interacts with, e.g., binds, IKK-β; an antibody, e.g., an intrabody or a randomly generated antibody which interacts with IKK-β; a small molecule, e.g., a small molecule which interacts with IKK-β.

In a preferred embodiment, the compound is a compound other than aspirin.

In another aspect, the invention features a method of treating a subject having a disorder characterized by insulin resistance. The method includes: administering a compound or agent which interacts with, e.g., binds, IKK-β, to thereby treat the disorder.

In a preferred embodiment, the disorder is diabetes, e.g., Type I or Type II diabetes, obesity, polycystic ovarian disease or syndrome X.

In a preferred embodiment, the compound is: a compound other than aspirin; a polypeptide, e.g., a randomly generated polypeptide which interacts with IKK-β; an antibody, e.g., an intrabody or a randomly generated antibody which interacts with IKK-β; a small molecule, e.g., a small molecule which interacts with IKK-β. In a preferred embodiment, the method includes administering a nucleic acid encoding one of the above-described compounds. In a preferred embodiment, the compound is a compound identified by a method described herein.

In a preferred embodiment, the compound is administered parenterally, e.g., intravenously, intradermally, subcutaneously, orally (e.g., inhalation). In a preferred embodiment, the administration of the compound is time-released.

In a preferred embodiment, the subject is a human. In another preferred embodiment, the subject is a NOD mouse, an ob/ob mouse, a db/db mouse, a Zucker fatty rat, or a streptozotocin induced rat.

In another aspect, the invention features a method of treating a subject having diabetes, e.g., Type I or Type II diabetes. The method includes administering to a subject a compound or agent which interacts with, e.g., binds, IKK-β, to thereby treat the diabetes.

In a preferred embodiment, the compound is: a compound other than aspirin; a polypeptide, e.g., a randomly generated polypeptide which interacts with IKK-β; an antibody, e.g., an intrabody, e.g., an anti-IKK-β antibody or a randomly generated antibody which interacts with IKK-β, a small molecule, e.g., a small molecule which interacts with IKK-β. In a preferred embodiment, the method includes administering a nucleic acid encoding one of the above-described compounds. In a preferred embodiment, the compound is a compound identified by a method described herein.

In a preferred embodiment, the compound is administered parenterally, e.g., intravenously, intradermally, subcutaneously, orally (e.g., inhalation). In a preferred embodiment, the administration of the compound is time-released.

In a preferred embodiment, the subject is a human. In another preferred embodiment, the subject is a NOD mouse, an ob/ob mouse, a db/db mouse, a Zucker fatty rat, or a streptozotocin induced rat.

In another aspect, the invention features compounds for the treatment of disorders characterized by insulin resistance, identified by the methods described herein.

The terms protein, polypeptide and peptide are used interchangeably herein.

A subject, as used herein, refers to a mammal, e.g., a human. It can also refer to an experimental animal, e.g., an animal model for an insulin-related disorder, e.g., a NOD mouse, an ob/ob mouse, a db/db mouse, a Zucker fatty rat, or a streptozotocin induced mouse or rat. The subject can be a human which is at risk for a disorder characterized by insulin resistance. Such disorders include diabetes, e.g., Type I or Type II, obesity, polycystic ovarian disease and syndrome X.

DETAILED DESCRIPTION OF THE INVENTION

Primary High-Through-Put Methods for Screening Libraries of Peptide Fragments

Various techniques are known in the art for screening gene libraries including existing gene libraries as well as generated mutant gene libraries. Techniques for screening large gene libraries often include cloning the gene library into replicable expression vectors, transforming appropriate cells with the resulting library of vectors, and expressing the genes under conditions in which detection of a desired activity, e.g., in this case, binding to IKK-β, facilitates relatively easy isolation of the vector encoding the gene whose product was detected. Each of the techniques described below is amenable to high through-put analysis for screening large numbers of sequences.

Two Hybrid Systems

Two hybrid (interaction trap) assays can be used to identify peptides which bind IKK-β (see e.g., U.S. Pat. No. 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., IKK-β or a fragment thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein IKK-β with another protein.

Display Libraries

In one approach to screening assays, the candidate peptides are displayed on the surface of a cell or viral particle, and the ability of particular cells or viral particles to bind IKK-β or a fragment thereof via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991)

Bio/Technology 9:1370–1371; and Goward et al. (1992) TIBS 18:136–140).

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

A common approach uses the maltose receptor of E. coli (the outer membrane protein, LamB) as a peptide fusion partner (Charbit et al. (1986) EMBO 5, 3029–3037). Oligonucleotides have been inserted into plasmids encoding the LamB gene to produce peptides fused into one of the extracellular loops of the protein. These peptides are available for binding to IKK-β. Other cell surface proteins, e.g., OmpA (Schorr et al. (1991) Vaccines 91, pp. 387–392), PhoE (Agterberg, et al. (1990) Gene 88, 37–45), and PAL (Fuchs et al. (1991) Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080–1083). Surface proteins of other bacterial species have also served as peptide fusion partners. Examples include the Staphylococcus protein A and the outer membrane protease IgA of Neisseria (Hansson et al. (1992) J. Bacteriol. 174, 4239–4245 and Klauser et al. (1990) EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein Lacd to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) Proc. Natl. Acad. Sci. U.S.A. 89–1869).

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) Proc. Natl. Acad. Sci. U.S.A. 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) J. Med. Chem. 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/ phagemid or plasmid libraries. Furthermore, the construction of the libraries, expression of the peptides, and screening, is done in an entirely cell-free format.

In one application of this method (Gallop et al. (1994) J. Med. Chem. 37(9):1233–1251), a molecular DNA library encoding $10^{12}$ decapeptides was constructed and the library expressed in an E. coli S30 in vitro coupled transcription/ translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Other Methods of Identifying Small Molecules which Interact with IKK-β

Computer-based analysis of a protein with a known structure can also be used to identify molecules which will bind to the protein. Such methods rank molecules based on their shape complementary to a receptor site. For example, using a 3-D database, a program such as DOCK can be used to identify molecules which will bind to IKK-β. See Des-Jarlias et al. (1988) *J. Med. Chem.* 31:722; Meng et al. (1992) *J. Computer Chem.* 13:505; Meng et al. (1993) *Proteins* 17:266; Shoichet et al. (1993) *Science* 259:1445. In addition, the electronic complementarity of a molecule to a targeted protein can also be analyzed to identify molecules which bind to the target. This can be determined using, for example, a molecular mechanics force field as described in Meng et al. (1992) *J. Computer Chem.* 13:505 and Meng et al. (1993) *Proteins* 17:266. Other programs which can be used include CLIX which uses a GRID force field in docking of putative ligands. See Lawrence et al. (1992) *Proteins* 12:31; Goodford et al. (1985) *J. Med. Chem.* 28:849; Boobbyeretal. (1989) *J. Med. Chem.* 32:1083.

Secondary Screens

The high through-put assays described above can be followed by secondary screens in order to identify further biological activities which will, e.g., allow one skilled in the art to differentiate agonists from antagonists. For example, a cell based assay can be used to identify compounds which have the ability to modulate, e.g., inhibit, IKK-β activity of a cell. For example, the ability of a compound to modulate, e.g., inhibit, insulin resistance in a cell in vitro or in vivo. Cultured cells which can be used to determine the effect of a compound on insulin resistance include liver and fat cells.

For in vivo testing of a compound to reduce or inhibit insulin resistance, the compound can be administered to an accepted animal model. Experimental models for insulin resistance include NOC mice, ob/ob mice, db/db mice, Zucker fatty rats and streptozotocin induced rats.

Once the core sequence of interest is identified, it is routine to perform for one skilled in the art to obtain analogs and fragments.

What is claimed:

1. A method of identifying a compound for treatment of insulin resistant diabetes or insulin resistant obesity, comprising;
   contacting a test compound with IKK-β;
   determining whether the test compound inhibits IKK-β kinase activity, and
   administering said test compound that inhibits IKK-β kinase activity to a subject having insulin resistant diabetes or insulin resistant obesity, thereby identifying a compound for the treatment of insulin resistant diabetes or insulin resistant obesity.

2. The method of claim 1, wherein determining whether the test compound inhibits IKK-β activity comprises determining the ability of the compound to bind the IKK-β polypeptide.

3. The method of claim 2, wherein determining whether the test compound inhibits IKK-β activity comprises detecting the formation of a complex between IKK-β and the compound.

4. The method of claim 1, wherein the compound is selected from the group consisting of a peptide, an antibody and a small molecule.

5. The method of claim 1, wherein the compound is contacted with an IKK-β polypeptide in the presence of aspirin.

6. The method of claim 1, wherein the subject is selected from the group consisting of a non-obese diabetic (NOD) mouse, an ob/ob mouse, a db/db mouse, a Zucker fatty rat, and a streptozotocin rat.

7. The method of claim 1, wherein the test compound is contacted with purified IKK-β polypeptide.

8. The method of claim 1, wherein the test compound is contacted with IKK-β polypeptide in a cell free assay.

9. A method of identifying a compound for treatment of insulin resistant diabetes or insulin resistant obesity, comprising;
   identifying a compound that inhibits IKK-β kinase activity; and
   determining the effect of the identified compound on insulin resistant diabetes or insulin resistant obesity in a subject, wherein the identified compound is identified a compound for the treatment of insulin resistant diabetes or insulin resistant obesity if it reduces insulin resistant diabetes or insulin resistant obesity.

10. The method of claim 9, wherein the subject is selected from the group consisting of a non-obese diabetic (NOD) mouse, an ob/ob mouse, a db/db mouse, a Zucker fatty rat and a streptozotocin rat.

11. The method of claim 9, wherein identifying a compound that inhibits IKK-β kinase activity comprises determining the ability of the compound to bind the IKK-β polypeptide.

12. The method of claim 9, wherein the compound is selected from the group consisting of a peptide, an antibody and a small molecule.

* * * * *

UNITED STATES PATENT AND TRADEMARK OFFICE
CERTIFICATE OF CORRECTION

PATENT NO.    : 6,468,755 B1
DATED         : October 22, 2002
INVENTOR(S)   : Steven Shoelson It is certified that error appears in the above-identified patent and that said Letters Patent is hereby corrected as shown below:

<u>Column 1,</u>
Line 4, before "CROSS REFERENCE TO RELATED APPLICATIONS", insert the following paragraph:

-- STATEMENT REGARDING FEDERALLY SPONSORED RESEARCH
This invention was made with support from the U.S. government under grant number DK 45493 awarded by the National Institutes of Health. The government has certain rights in the invention. --.

Signed and Sealed this

Fourth Day of March, 2003

JAMES E. ROGAN
*Director of the United States Patent and Trademark Office*